United States Patent [19]
Hirano

[11] Patent Number: 4,674,743
[45] Date of Patent: Jun. 23, 1987

[54] ATHLETIC TRAINING UNIT WITH MUSICAL RHYTHM REPRODUCING SPEAKER AND EXERCISER'S PULSE DETECTING MEANS

[75] Inventor: Mutsuo Hirano, Saitama, Japan

[73] Assignee: Sanden Corporation, Gunman, Japan

[21] Appl. No.: 774,913

[22] Filed: Sep. 11, 1985

[30] Foreign Application Priority Data

Sep. 12, 1984 [JP] Japan .................. 59-137148[U]
Mar. 1, 1985 [JP] Japan .................. 60-27991[U]
Mar. 1, 1985 [JP] Japan .................. 60-27992[U]

[51] Int. Cl.⁴ .................................. B25J 1/00
[52] U.S. Cl. .................. 272/100; 272/DIG. 9; 368/10; 340/323 R
[58] Field of Search .................. 272/100, DIG. 9; 368/10; 340/323 R

[56] References Cited

U.S. PATENT DOCUMENTS 3,492,582  1/1970  Heywood .................. 272/100
3,846,704  11/1974  Bessette .................. 368/10

OTHER PUBLICATIONS

"*Heart Computer*", ad from Nov. 1980 Popular Science magazine.

*Primary Examiner*—Leo P. Picard
*Attorney, Agent, or Firm*—Hopgood, Calimafde, Kalil, Blaustein & Judlowe

[57] ABSTRACT

An athletic training unit having a radio receiver and speakers for informing a music and instructor's messages to an exerciser by a wireless manner. A desired rhythm signal is selectively supplied to the speakers from a rhythm generator so as to provide the musical rhythm to the exerciser. The unit further has a sensor for detecting the pulse of the exerciser so that the exerciser is noticed a fact that his pulse exceeds his safety upper limit for exercising. As the pulse sensor, a pair of an infrared LED and a photo transistor is used.

17 Claims, 13 Drawing Figures

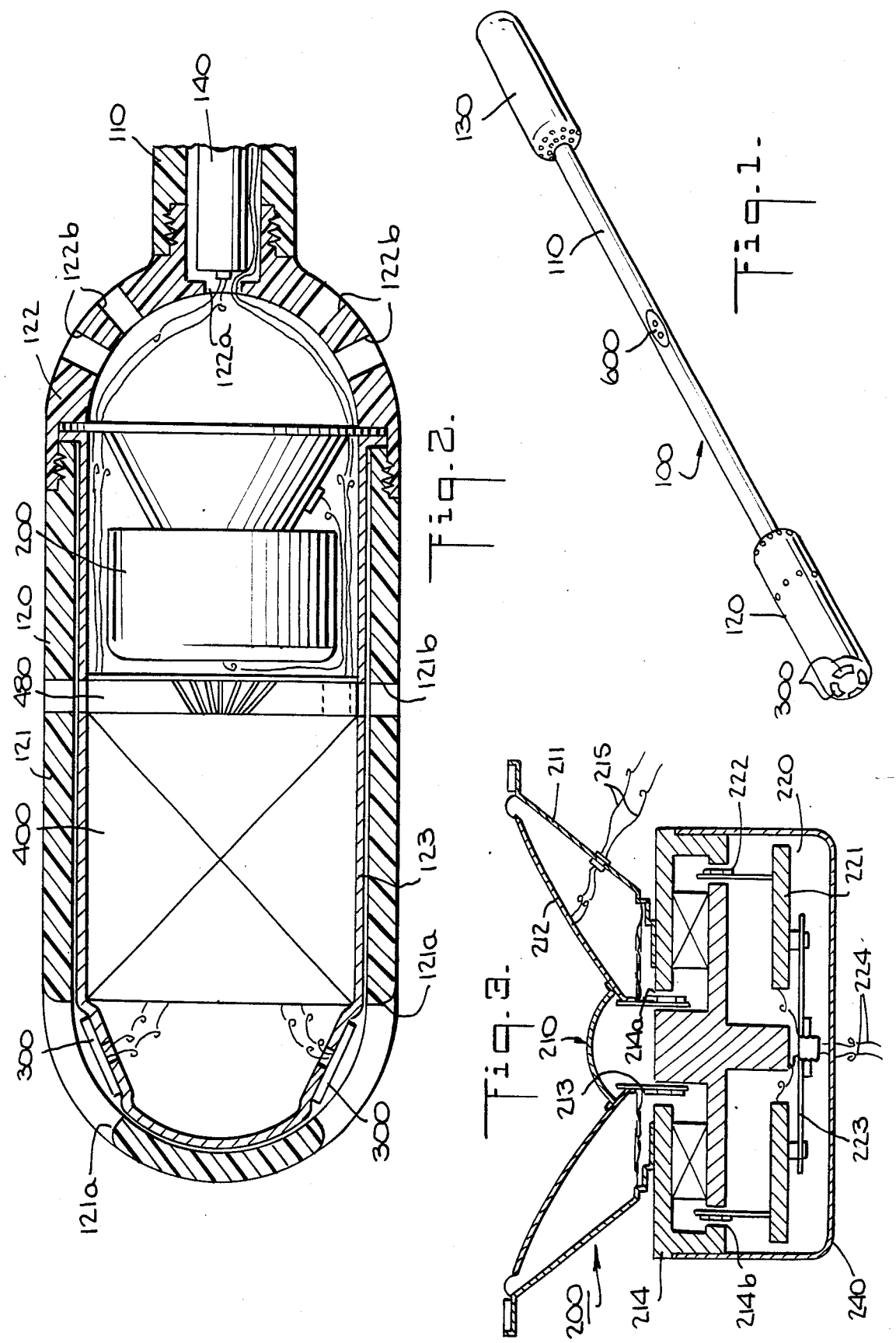

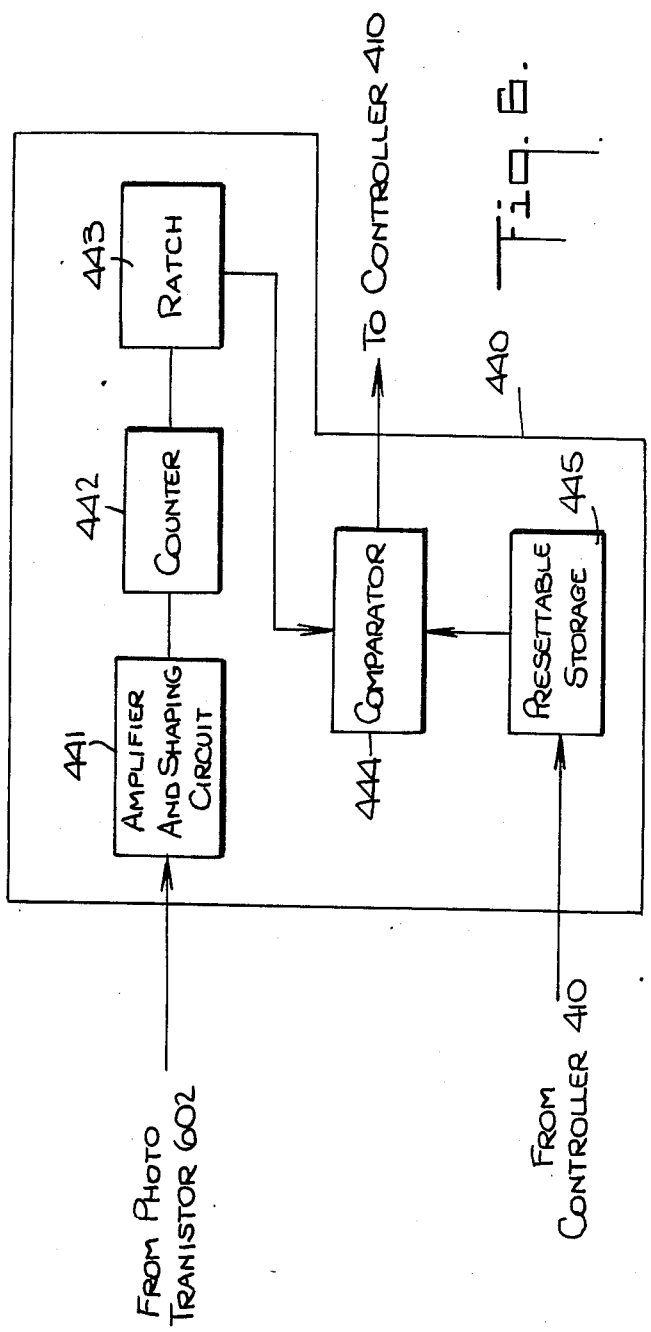
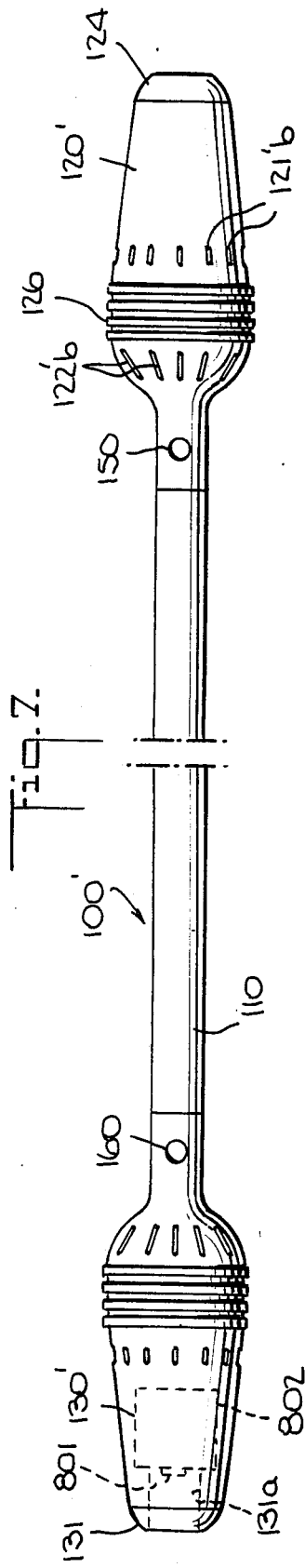

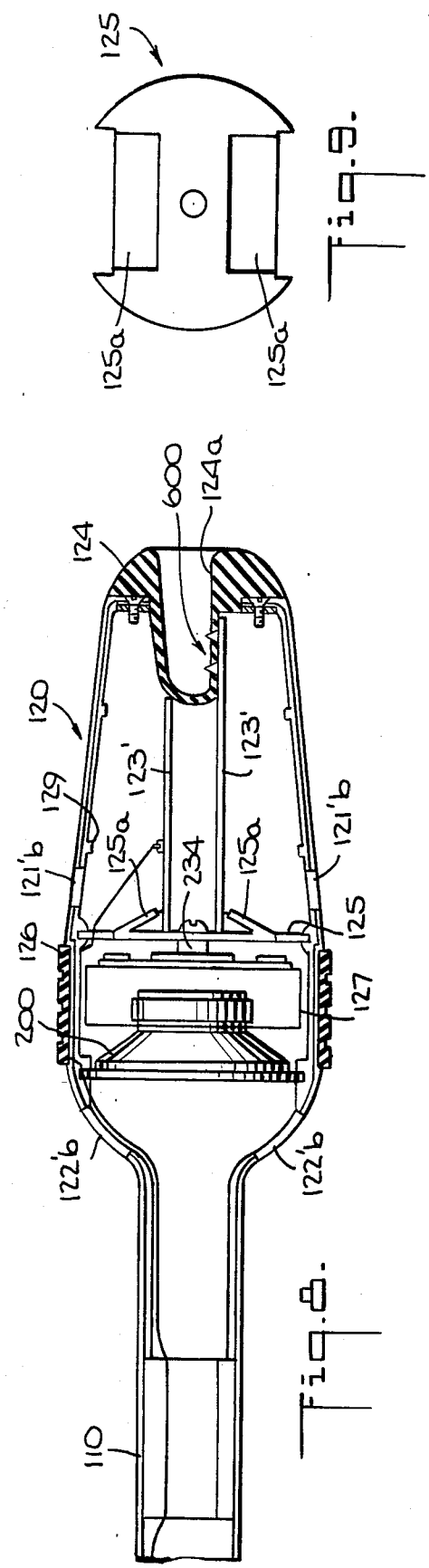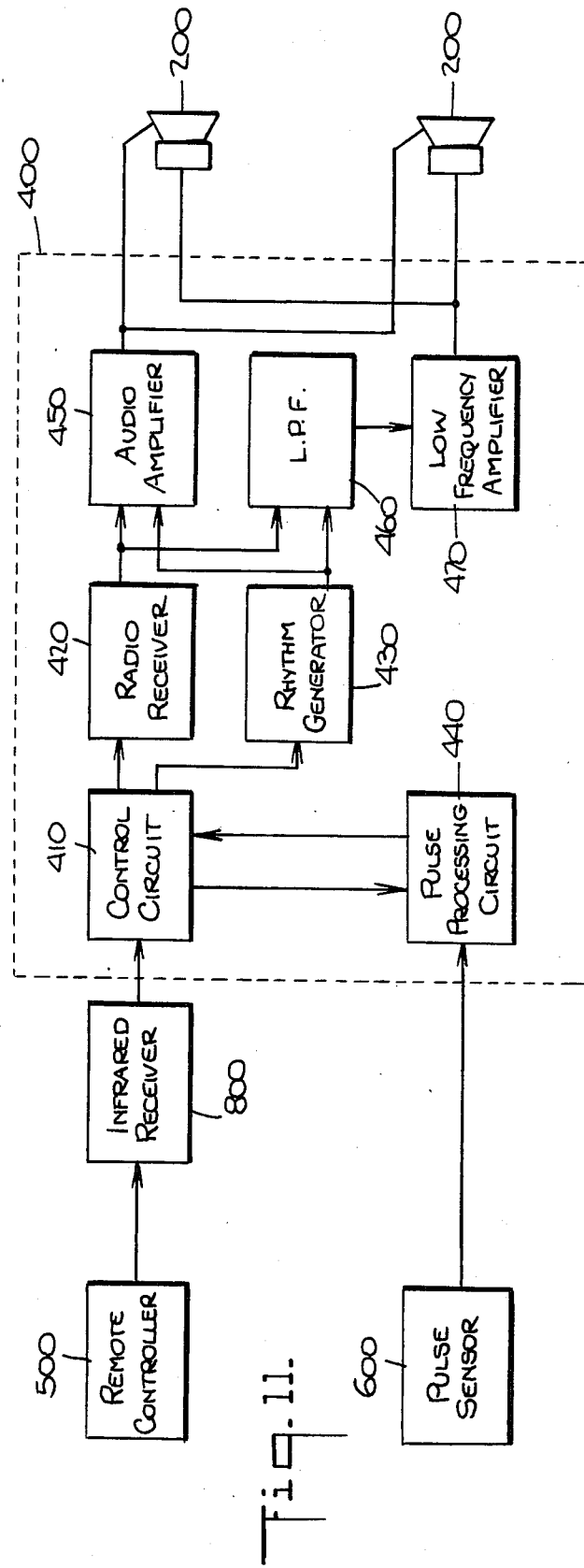

ATHLETIC TRAINING UNIT WITH MUSICAL RHYTHM REPRODUCING SPEAKER AND EXERCISER'S PULSE DETECTING MEANS

BACKGROUND OF THE INVENTION

1. Field of the Invention

The present invention relates to athletic training aids for exercisers, and in particular, to athletic training units being suitable for the exerciser's personal use to listen his instructor's comments and/or musical rhythm during his exercising and to know his physical limit for exercise.

2. Description of the Prior Art

Music is used in various athletic exercises such as aerobics dance, jazz dance and others. In training, the music is radiated from a speaker or speakers installed in the training room, and instructor's comments are given to trainees directly or through the speakers. However, trainees have a difficulty to listen to the music and the instructor's comments because of noise caused by the trainees' exercising, especially, during group exercising.

Everyone has an individual safety limit for physical exercise depending on his physical strength, age, health and others. The exerciser's pulse or heart beat number increases by his exercising. It is dangerous for the exerciser to maintain the exercise after his pulse increases to his safety limit.

SUMMARY OF THE INVENTION

It is an object of the present invention to provide an athletic training unit suitable for personal use of an exerciser which enables the exerciser to easily listen music and/or instructor's comments at hand and to know his pulse increasing to his safety limit during the exercise.

It is another object of the present invention to provide such an athletic training unit which can be also used as a hand apparatus for exercises.

It is still another object of the present invention to provide the athletic training unit wherein a desired music rhythm can be generated by the user's selection.

According to the present invention, an athletic training unit is obtained which is suitable for individual use of an exerciser. The unit comprises means for generating an audio signal, electro-acoustic transducer means for transducing the audio signal into sound, and electric vibrator means for reproducing undertone vibrator of the audio signal.

The unit further comprises means for sensing the pulse of the exerciser using the unit, presettable storage means for storing a preset upper limit of the pulse, and means for comparing the sensed pulse from the pulse sensing means with the preset upper limit of the pulse. The comparing ing means generates a warning signal at a time when the sensed pulse reaches to, or exceeds, the preset upper limit of the pulse. The exerciser is alarmed by an alarm means in response to the warning signal.

The audio signal generating means, the electroacoustic transducer means, the electric vibrator means, the pulse sensing means, the presettable storage means, the comparing means, and the alarm means are mounted in a housing. According to an aspect, the housing is a lengthy stick-like housing.

According to another aspect, the audio signal generating means comprises a radio receiver receiving a radio signal carrying a music and instructor's messages and radiated from a radio transmitter installed in, for example, a training room.

According to still another aspect, the audio signal generating means comprises musical rhythm generator means for generating a musical rhythm signal such as waltz, beguine, bossa nova, rock-'n'-roll, march, or others. The unit is provided with rhythm selecting means for selecting one of different rhythms.

According to yet another aspect, the unit is accompanied with a separate remote controller unit by which the radio receiver, the rhythm generator, the presettable storage means and/or pulse sensing means can be controlled.

As an example of the pulse sensing means, a pair of a light source emitting a light of a wavelength of 0.6–1.9 μm and a photoelectric device. The light emitted from the light source is reflected by the hemoglobin in blood, and sensed by the photo-electric device. The reflected light strength is dependent on concentration of the hemoglobin. Therefore, the exerciser's pulse can be sensed by application of the light source-photoelectric device pair to the skin of the exerciser.

Further objects, features and other aspects will be understood from the following detailed description of preferred embodiments with reference to the accompanying drawings.

BRIEF DESCRIPTION OF THE DRAWINGS

FIG. 1 is a perspective view of an athletic training unit according to an embodiment of the present invention;

FIG. 2 is a sectional view of a case portion of the unit of FIG. 1;

FIG. 3 is a sectional view of a speaker device used in the unit;

FIG. 6 is a schematic circuit diagram view of a pulse processing circuit in FIG. 4;

FIG. 7 is a partially broken perspective view of a modified embodiment;

FIG. 8 is a sectional view of a case portion of the unit in FIG. 7;

FIG. 9 is a side view of a heat sink assembled in the case portion in FIG. 8;

FIG. 11 is a schematic circuit diagram view of an electric circuit in the unit of FIG. 7;

DETAILED DESCRIPTION OF PREFERRED EMBODIMENTS

Figure 4:
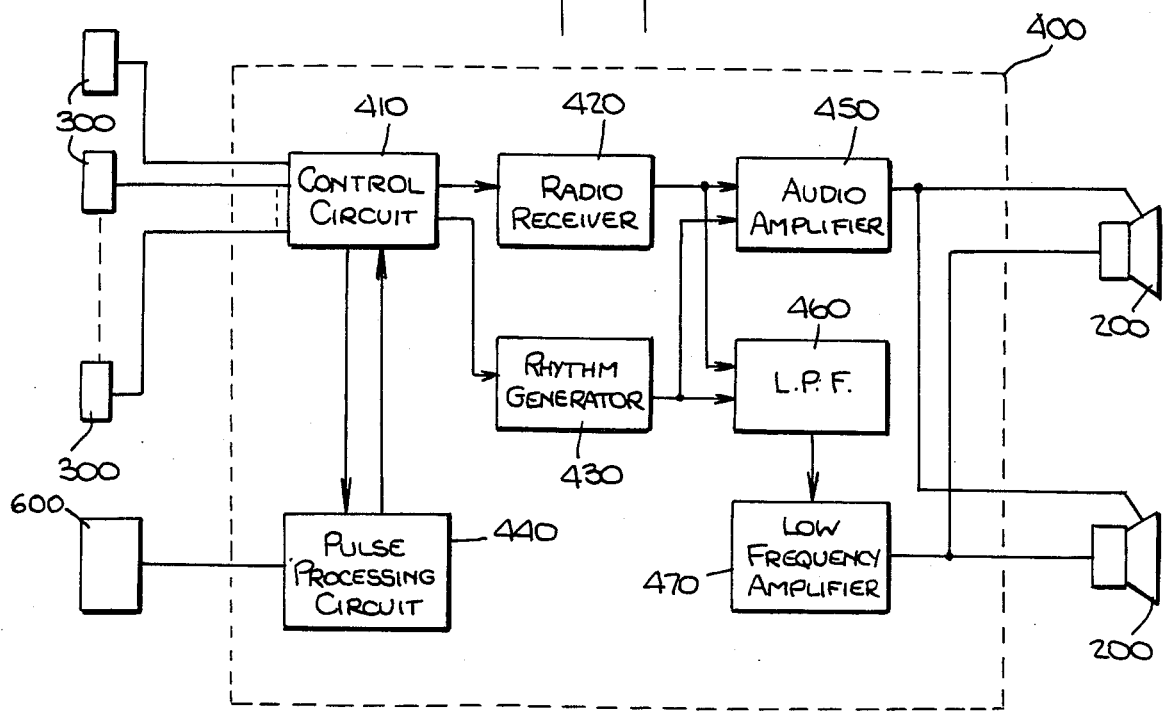
FIG. 4 is a schematic circuit diagram view of an electric circuit in the unit.

Referring to FIG. 1, an embodiment shown therein is an elongated unit 100 which can be used as a hand apparatus by an exerciser.

The unit 100 comprises a shaft portion 110 of a hollow plastic tube. Two thick plastic cases 120 and 130 are mounted on opposite ends of shaft portion 110.

Referring to FIG. 2, case 120 comprises a main portion 121 with an open end and a cap portion 122 removably connected to the open end of main portion 121.

The other end of cap portion 122 is removably mounted onto one end of shaft portion 110. The interior of the case 120 is communicated with the hollow interior of shaft portion 110 through a central opening 122a of cap portion 122. In main portion 121 is mounted a chassis 123 on which a speaker 200, a plurality of selection switches 300 and an electric circuit component 400 are mounted. Main portion 121 of case 120 is provided with a plurality of apertures 121a for exposing selection switches 300 so that selection switches can be manually operated outside case 120.

The other case 130 can be comprised of a main portion and a cap portion similar to case 120, and is provided with a chassis and speaker. In some cases, several selection keys 300 and a certain portion of the electric circuit component 400 can be provided in the other case 130. The case 130 can be understood from the above description referring to FIG. 2, without any sectional view of the case 130.

In the hollow interior of shaft 110, an electric power source such as electric cells 140 and a sensor 600 (see FIG. 1) for sensing the exerciser's pulse are mounted, which are connected to electric circuit component 400 through electric wires.

Referring to FIG. 3, speaker 200 has a dynamic speaker 200 which comprises a frame 211, a vibrating plate 212, a voice coil 213, a magnetic circuit structure 214 having a magnetic gap 214a for voice coil 213, and lead wires 215. The speaker 200 is additionally provided with a vibrating component 220 for reproducing mechanical undertone vibration. The vibrating component 220 comprises a weight plate 221 in the form of a flat annular plate, another voice coil 222 mounted thereto, and a spring plate 223 supporting weight plate 221. The magnetic circuit structure 214 is provided with an additional magnetic gap 214b in which the another voice coil 222 is disposed. The voice coil 222 is connected to the electric circuit component through electric wires 224. The vibrating component 220 is covered with a cover 240.

On application of an audio signal to the speaker 200 from circuit component, dynamic speaker 210 reproduces sound which is radiated outside the case 120 through a plurality of openings 122b in cap 122 (see FIG. 2). The vibrating component 220 reproduces the undertone vibration which is transferred to case 120 and shaft 110 through magnetic circuit structure 214, frame 211, and chassis 123.

Figure 10:
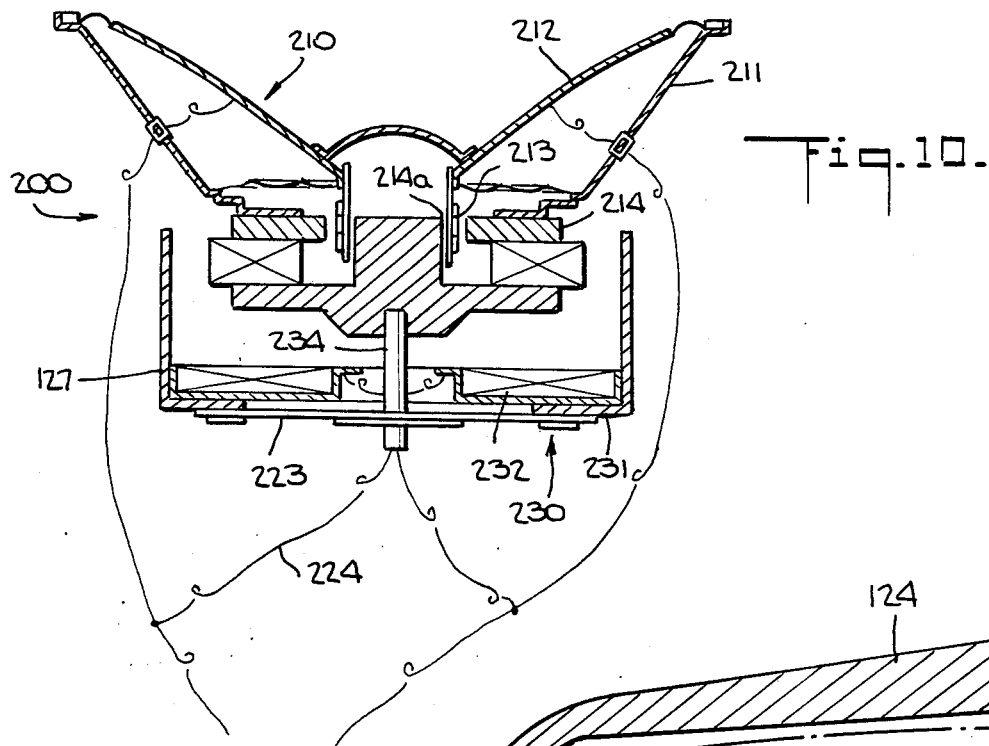
FIG. 10 is a sectional view of another speaker device used in the unit.

Another speaker arrangement can alternatively be used, for example, which is shown in FIG. 10.

Referring to FIG. 4, the electric circuit component 400 comprises a control circuit 410, a radio receiver 420, a rhythm generator 430, a pulse processing circuit 440, an audio amplifier 450, a low-pass filter 460 and a low frequency amplifier 470.

Control circuit 410 receives selection signals from selection switches 300 and supplies predetermined control signals to radio receiver 420, rhythm generator 430 and/or pulse processing circuit 440.

Radio receiver 420 starts by a start signal from control circuit 410 in response to operation of a radio receiver selecting one of selection switches 300. Radio receiver 420 receives a radio signal carrying music and/or instructor's message which is radiated from a transmitter installed in a training room or studio. Radio receiver 420 detects music signal and message signal, which is, in turn, amplified at audio amplifier 450 and then supplied to the dynamic speaker (210 in FIG. 3) of speakers 200. The detected signal is also applied to low-pass filter 460 at which an undertone component is derived. The undertone component is amplified at low frequency amplifier 470, and is then applied to the vibrating component 220 of speaker 200. Thus, the beats representing rhythm of the music are reproduced by vibrating component 220 as mechanical vibrations.

Rhythm generator 430 generates a rhythm signal representing a pattern of recurrence of beats of a musical rhythm such as beguine, bossa nova, rock-'n'-roll, march, waltz or other rhythm identified by the control signal from control circuit 410 in response to operation of one of selection switches 300. The rhythm signal from rhythm generator 430 is supplied to speakers 200 through audio amplifier 450 and low-pass filter and low frequency amplifier 460–470, respectively, in the similar manner as the signal from radio receiver 420.

As an example of such a rhythm generator, a MOS-type integrated circuit "LM 8972" can be available in commerce which is made and sold by SANYO, a Japanese corporation. A microprocessor can be used as the rhythm generator by providing a proper program.

The pulse processing circuit 440 will be described hereinafter.

Two amplifiers 450 and 470 are provided with a heat sink 480 as shown in FIG. 2. Heat generated by the amplifiers is transferred through the heat sink 480 and is radiated in atmosphere through apertures 121b in main portion 121 of case 120.

Figure 5:
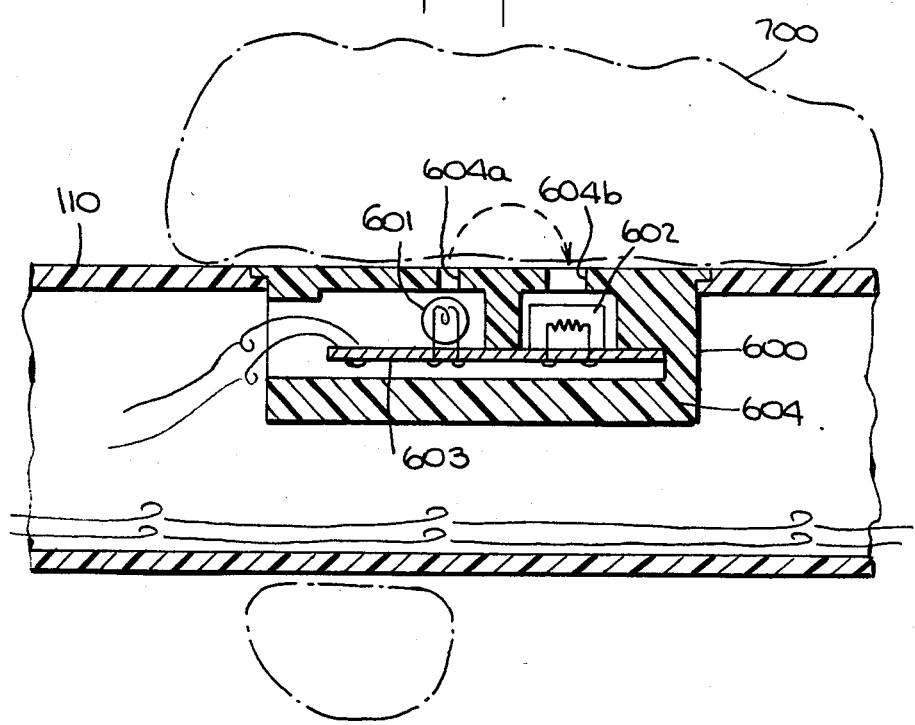
FIG. 5 is an enlarged sectional view for illustrating a pulse sensor in the unit.

Referring to FIG. 5, pulse sensor 600 comprises a light source 601 such as a light emission diode (LED), preferably emitting the infrared light, and a photoelectric device 602 such as a photo transistor or diode. The LED 601 and the photo transistor 602 are mounted on a printed circuit board 603 which is fixedly mounted within a small housing 604 mounted in shaft portion 110. The small housing 604 is provided with two windows 604a and 604b in front of LED 601 and photo transistors 602.

The light emitted from LED 601 is radiated through window 604a to a skin of a hand 700 grasping a region of the shaft 110 including the sensor 600. The light is reflected by hemoglobin in blood flowing in the skin and is received by photo transistor 602 through window 604b. The reflected light strength is dependent on the amount of the hemoglobin. Therefore, the electric current outputted from photo transistor 602 varies in dependence of pulsations of the exerciser, that is, the exerciser's pulse can be detected as an electric pulse signal.

Referring to FIG. 6, pulse processing circuit 440 comprises a pulse wave amplifying and shaping circuit 441 for amplifying and shaping the pulse signal outputted from photo transistor 602. The pulses as amplified and shaped at circuit 441 are counted up at counter 442 for a predetermined unit time such as one minute. The number counted up for the predetermined unit time is transferred to ratching circuit 443 and is ratched thereat. At the moment, counter 442 is cleared and then restarts its pulse counting operation.

A safety upper limit of the exerciser's pulse can be previously stored by using one of selector switch 300 through control circuit 410.

The number ratched at ratching circuit 443 is compared with the stored safety upper limit of the exerciser's pulse at a comparator 444. When the former is smaller than the latter, the output of the comparator 444 is maintained at a low level signal. On the contrary, when the former is equal to, or exceeds, the latter, the comparator 444 outputs a high level signal, that is, a warning signal. Then, control circuit 410 stops operation of radio receiver 420 and rhythm generator 430. The exerciser is notified by silence of speakers 200 that he should stop his exercising. Alternatively, control circuit 410 controls rhythm generator 430 to generate alarm from speakers 200.

According to the embodiment of FIGS. 1-6, the exerciser can use the unit 100 as a hand apparatus for his exercise, and can exercise rhythmically listening music or musical rhythm radiated from speakers 200 and feeling rhythmical vibration of the unit without interference by noise. When the radio receiver 410 is selected by one of selection switches 300, the exerciser can also listen the instructor's messages through speakers 200.

Furthermore, since the exerciser's pulse is sensed during his exercising if he grasps sensor portion 600 of shaft 110 by hand (700 in FIG. 5), and since he is notified when his pulse reaches his own safety upper limit, he can stop his exercising without over exercise which may be dangerous for his body.

A modification is shown in FIGS. 7-13. Referring to FIG. 7, a unit 100' shown therein comprises a plastic shaft portion 110 and plastic cases 120' and 130' mounted on opposite ends thereof similar to the unit of FIG. 1.

Referring to FIG. 8, plastic case 120' is provided with a rubber element 124 mounted on a top end thereof. Rubber element 124 has a hollow opening 124a into which a human finger, for example, an index finger can be inserted.

In the case 120' is mounted a chassis 123' on which an electric circuit component (400 in FIG. 11), a heat sink 125, a speaker 200, and a pulse sensor 600 are mounted.

Referring to FIG. 9, heat sink 125 is a generally circular plate with bent flanges 125a.

Heat sink 125 is attached to chassis 123', and speaker 200 is mounted on heat sink 125.

Case 120' is provided with slits 122'b and 121'b corresponding to openings 122b and 121b in FIG. 2, and is provided with a rubber tube 126 fitted on the outer surface of the case around speaker 200.

Speaker as shown in FIG. 3 can be used as the speaker 200. However, this modification uses a speaker as shown in FIG. 10.

Referring to FIG. 10, speaker 200 comprises a dynamic speaker 210 comprising a frame 211, a vibrating plate 212, a voice coil 213, a magnetic circuit structure 214 with a magnetic gap 214a for the voice coil, and electric wires 215.

The speaker 200 is further provided with a vibrating component 230 which comprises an annular coil housing 231, a coil 232, and a spring plate 233 elastically supporting the coil housing. The spring plate 233 is fixedly mounted on a supporting rod 234 mounted on magnetic circuit structure 214. Another heat sink 127 for the speaker is mounted on coil housing. Lead wires 224 from coil 232 are connected to the electric circuit component (400 in FIG. 11).

Referring to FIG. 11, the electric circuit component 400 is similar to the component 400 as shown in FIG. 4 and comprises control circuit 410, radio receiver 420, rhythm generator 430, pulse processing circuit 440, audio amplifier 450, low-pass filter 460 and low frequency amplifier 470.

As described above in connection with FIG. 4, an audio signal is applied to speakers 200 from audio amplifier 450 and sound is radiated from speakers 200. While, a low frequency signal is applied from low frequency amplifier 470 to vibrating component 230 of each speaker 200.

Referring to FIG. 10 again, when the low frequency signal flows through coil 232, A.C. magnetic field is produced in a D.C. magnetic field leaking from magnetic circuit structure 214. Accordingly, the vibrating component 230 vibrates. Thus, the undertone mechanical vibration is produced and is transferred to case 120, 130 and shaft 110 through heat sink 125 and chassis 123'.

One of two speakers 200 in FIG. 11 is mounted in another case 130 in similar manner as shown in FIG. 8.

Although selection switches 300 are mounted in case 120 in the embodiment of FIGS. 1-6, they are provided in a separate unit or a remote controller 500.

Figure 12A:
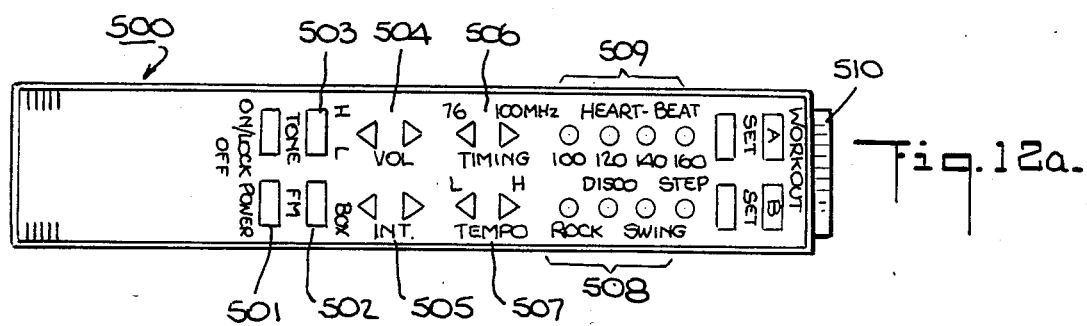
FIGS. 12a and 12b are a front view and a side view, respectively, of a remote controller used together with the unit of FIG. 7.
Figure 12B:
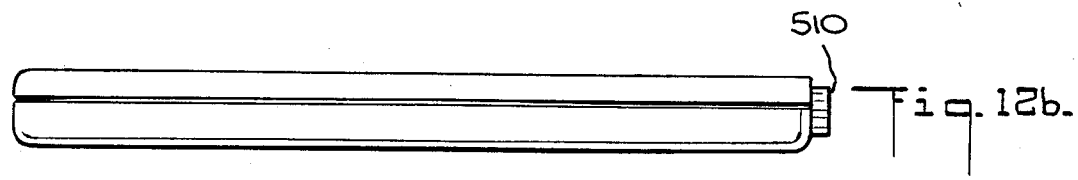

Referring to FIGS. 12a and 12b, remote controller 500 is provided with a power switch 501, a selection switch 502 for selecting either one of radio receiver 420 and rhythm generator 430, a tone adjusting switch 503, volume switches 504 for the radio receiver, beat intensity adjusting switches 505 for the rhythm generator, frequency selection switches 506 for the radio receiver, rhythm tempo adjusting switches 507 for the rhythm generator, rhythm selection switches 508, and buttons 509 for presetting a safety upper limit of the exerciser's pulse.

A signal in response to operation of any one of these switches 501-509 is transmitted to unit 100' by the use of a known modulation method of a carrier wave such as an infrared ray. In FIG. 12, the remote controller 500 is shown to be provided with an infrared ray projecting window 510.

Referring to FIG. 11 again, an infrared ray receiver 800 is provided for receiving the infrared ray from remote controller 500. The receiver 800 demodulates the signal corresponding to operated one of switches 501-509 in a known demodulating manner, and the demodulated signal is applied to control circuit 410. The control circuit 410, then, controls radio receiver 420, rhythm generator 430 and pulse processing circuit 440 in the similar manner as in FIG. 4.

Referring to FIG. 7, the infrared receiver 800 is mounted in case 130' and comprises a photoelectric device such as a photo transistor 801 and a receiver circuit 802. Case 130' is also provided with a rubber element 131 on one end. The rubber element 131 has an opening 131a in which the photo transistor 801 is disposed.

Figure 13:
FIG. 13 is an enlarged sectional view of a pulse sensor portion of the unit in FIG. 7.

Referring to FIGS. 8 and 13, pulse sensor 600 comprises LED 601 and photo transistor 602 similar to that as described above in connection with FIG. 5. The pulse sensor 600 is mounted on chassis 123' so that LED 601 and photo transistor 602 are exposed in hollow opening 124a of rubber element 124.

When the exerciser inserts his finger, for example, index finger 700' into opening 124a as shown in FIG. 13, the light emitted from LED 601 is reflected by hemoglobin in blood flowing in the finger, and the reflected light is received by photo transistor. Thus, the exerciser's pulse can be sensed in the similar manner as described above in connection with FIG. 5.

The output signal from sensor 600 is supplied to pulse processing circuit 440 in FIG. 11 which comprises a circuit arrangement similar to FIG. 6, and is processed in the similar manner as described above in connection with FIG. 6.

When the sensed exerciser's pulse reaches to or exceeds the preset upper limit, the exerciser is also notified by stop of speakers or alarm generated by the rhythm generator. However, an alarm lamp 150 can be mounted on the shaft 110 as shown in FIG. 7 and can be turned on.

Referring to FIG. 7, the unit 100' may be provided with a power indicator 160 on the shaft portion 110 for indicating a power-on condition.

The present invention has been described in connection with embodiments which are a hand apparatus stick type. However, the present invention can be practiced in a small case type which the user can wear by the use of a belt or a cord. Alternatively, it can be also embodied in a comparatively large box type which is used on a floor near the exerciser.

What is claimed is:

1. An athletic training unit for use by an exerciser comprising in combination: first means for generating an audio signal; electro-acoustic transducer means coupled responsively to said first means for transducing the audio signal into sound; pulse sensing means for sensing the pulse of an exerciser using said unit; presettable storage means for storing a preset upper limit for said pulse; means coupled to said pulse sensing means and to said presettable storage means for comparing the sensed pulse from said pulse sensing means with said preset upper limit for said pulse, said comparing means generating a warning signal when the sensed pulse exceeds said preset upper limit of the pulse; means for communicating to said exerciser said warning signal; a housing having a hollow chamber containing said first means, said electro-acoustic transducer means, said pulse sensing means, said presettable storage means, said comparing means, and said alarm means therein; and electric vibrator means within said housing chamber coupled to said first means and to said housing for communicating to said housing undertone vibration corresponding to said audio signal.

2. The athletic training unit as claimed in claim 1, wherein said first means comprises a radio receiver means for receiving a radio signal training instructor's messages.

3. The athletic training unit as claimed in claim 1, which further comprises means for generating a rhythm selecting signal, and said audio signal generating means comprising rhythm signal generating means for generating a rhythm signal, said rhythm signal comprising electric pulses having a pulse occurrence pattern corresponding to a pattern of recurrence of beats of a musical rhythm identified by said rhythm selecting signal.

4. The athletic training unit as claimed in claim 3, wherein said audio signal generating means further comprises a radio receiver means for receiving a radio signal, and which further comprises a selection switch means for selecting one of said radio receiver means and said rhythm generator means.

5. The athletic training unit as claimed in claim 4, which further comprises switch means for inputting a safety upper limit of a user's pulse to preset the upper limit into said presettable storage means.

6. The athletic training unit as claimed in claim 5, which is accompanied with a remote controller which comprises rhythm selecting switch means, said selection switch means and said inputting switch means and means for radiating an infrared light carrying a signal in response to operation of one of said rhythm selecting switch means, said selection switch means and said inputting switch means, said athletic training unit further comprising an infrared light receiving means for detecting the signal carried on the infrared light as received thereat.

7. The atheletic training unit as claimed in claim 4, which further comprises a low-pass filter for removng a high frequency component of an audio signal from one of said radio receiver means and said rhythm generator means, and means for coupling an output signal of said low-pass filter to said vibrator means for reproducing said undertone vibration.

8. The athletic training unit as claimed in claim 1, wherein said pulse sensing means comprises light source means for emitting a light of a wavelength of 0.6–1.9 μm to the physical body of the exerciser, and photoelectric means for receiving the light reflected by hemoglobin in the blood flowing in the human body.

9. The athletic training unit as claimed in claim 8, wherein said light source means is an infrared light emission diode, and said photoelectric means is a photo transistor.

10. The athletic training unit as claimed in claim 1, wherein said vibrator means comprises coil means, weight plate means supporting said coil means, and spring plate means for elastically supporting said weight means, and wherein said vibrator means is mounted on said electroacoustic transducer means.

11. The athletic training unit as claimed in claim 1, wherein said warning communicating means comprises control means for stopping operation of said audio signal generating means in response to said warning signal, whereby the sound generation by said electro-acoustic transducer means is stopped to thereby warn the exerciser.

12. The athletic training unit as claimed in claim 1, wherein said warning communicating means comprises a warning lamp which turns on in response to said warning signal.

13. The athletic training unit as claimed in claim 1, wherein said housing comprises a thin hollow tubular portion adaptable for grasping by hand and a pair of cylindrical case portions mounted on opposite ends of said tubular portion, each cylindrical case portion having a diameter greater than said tubular portion.

14. The athletic training unit as claimed in claim 13, wherein said electro-acoustic transducer means comprises two speaker devices disposed in said paired cylindrical case portions, respectively.

15. The athletic training unit as claimed in claim 14, wherein said pulse sensing means is mounted in said tubular portion.

16. The athletic training unit as claimed in claim 14, wherein one of said case portions is provided with a hollow opening for receiving a human finger, and said pulse sensing means is disposed in the hollow opening.

17. The athletic training unit as claimed in claim 14, wherein each case is provided with heat sink means therein and a plurality of heat radiating apertures.

* * * * *

UNITED STATES PATENT AND TRADEMARK OFFICE
CERTIFICATE OF CORRECTION

PATENT NO. : 4,674,743

DATED : June 23, 1987

INVENTOR(S) : Mutsuo Hirano

It is certified that error appears in the above-identified patent and that said Letters Patent are hereby corrected as shown below:

In column 7, lines 40 and 41, "training instructor's messages" should be deleted.

Signed and Sealed this

Third Day of November, 1987

Attest:

DONALD J. QUIGG

Attesting Officer

Commissioner of Patents and Trademarks